United States Patent [19]

Kagara et al.

[11] Patent Number: 6,013,653
[45] Date of Patent: Jan. 11, 2000

[54] PROCESSES FOR PRODUCING PYRIDOINDOLE DERIVATIVES

[75] Inventors: Kooji Kagara, Mino; Nobutaka Kawai, Osaka; Takashi Nakamura, Nishinomiya; Shigeru Ieda, Takarazuka; Koji Machiya, Kobe; Atsushi Ohigashi, Kyoto, all of Japan

[73] Assignee: Fujisawa Pharmaceuticals Co., Ltd., Osaka, Japan

[21] Appl. No.: 09/043,121

[22] PCT Filed: Sep. 18, 1996

[86] PCT No.: PCT/JP96/02692

§ 371 Date: Apr. 21, 1998

§ 102(e) Date: Apr. 21, 1998

[87] PCT Pub. No.: WO97/11074

PCT Pub. Date: Mar. 27, 1997

[30] Foreign Application Priority Data

Sep. 22, 1995 [JP] Japan .................................. 7-269154
Nov. 20, 1995 [JP] Japan .................................. 7-326588

[51] Int. Cl.$^7$ ........................ A61K 31/44; A61K 31/435; C07D 221/06
[52] U.S. Cl. ............................ 514/294; 546/94; 546/95; 546/96
[58] Field of Search .............................. 514/294; 546/94, 546/95, 96

[56] References Cited

PUBLICATIONS

New 5HT3 (Serotin–3) receptor Antagonist II. Chem .Pharm. Bull. vol. 42 (12) pp. 2556–2564; by Masyuki Kato et al, Aug. 18, 1994.

New 5HT3 (Serotin–3) receptor Antagonist I. Chem .Pharm. Bull. vol 42 (12) pp. 2546–2555; by Masyuki Kato et al, Aug. 18, 1994.

New 5HT3 (Serotin–3) receptor Antagonist III. Chem .Pharm. Bull. vol. 43 (8) pp. 1346–1350; by Masyuki Kato et al, Apr. 4, 1995.

*Primary Examiner*—Alan L. Rotman
*Assistant Examiner*—Rita Desai
*Attorney, Agent, or Firm*—Oblon, Spivak, McClelland, Maier & Neustadt, P.C.

[57] ABSTRACT

A process for producing pyridiondole derivatives represented by general formula (III) or their salts (wherein $R^1$ represents hydrogen, lower alkyl or lower alkenyl; $R^2$ represents hydrogen, lower alkyl or halogeno; and $R^3$ represents optionally substituted imidazolyl), which comprises reacting a compound represented by general formula (I) or its salt (wherein $R^1$ and $R^2$ are each as defined above) with a compound represented by general formula (II) or its salt (wherein $R^3_a$ represents optionally substituted imidazolyl having an imino protecting group; and X represents halogeno), followed by a reaction for eliminating the imino protecting group); and a process for producing optically active pyridoindole derivatives represented by general formula (IV) or their salts: which comprises reacting a racemic mixture of the pyridoindole derivative represent by formula (III) or its salt with (1R)-(–)-10-camphorsulfonic acid.

4 Claims, No Drawings

PROCESSES FOR PRODUCING PYRIDOINDOLE DERIVATIVES

CROSS REFERENCE

This application is a 371 of PCT/JP96/02692 filed Sep. 18, 1996.

TECHNICAL FIELD

This invention relates to processes for the preparation of pyridoindole derivatives and salts thereof which are pharmaceutically effective as a 5-hydroxytryptamine (5-HT) antagonism.

BACKGROUND ART

Some pyridoindole derivatives indicated by the following general formula (III) and salts thereof are publicly known in the Japanese Kokai Tokkyo Koho 2-117675. These pyridoindole derivatives and salts thereof possess a 5-HT antagonism and are effective in the treatment and the prevention of central nervous system (CNS) disorders such as psychosis (e.g., schizophrenia, mania, etc.), anxiety, depression and so forth; pains such as headaches (e.g., migraine headaches, cluster headaches, vascular headaches, etc.), neuralgia (e.g., trigeminal neuralgia, etc.) and so forth; gastrointestinal disorders such as symptoms of gastrointestinal dysfunction accompanying dyspepsia, peptic ulcer, reflux esophagitis, meteorism, and the like, irritable bowel syndrome (IBS), and the like; nausea or vomiting accompanying cancer treatment; motion sickness; and so forth.

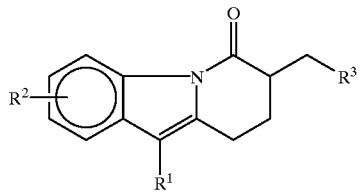

(III)

wherein $R^1$ is hydrogen, a lower alkyl group or a lower alkenyl group, $R^2$ is hydrogen, a lower alkyl group or a halogen, and $R^3$ is an imidazolyl group which may have a suitable substituent (s).

A process for the synthesis of (±)-8,9-dihydro-10-methyl-7-[(5-methyl-1H-imidazol-4-yl)methyl]pyrido[1,2-a]indol-6(7H)-one (IIIa) is described in Japanese Kokai Tokkyo Koho 2-117675 through the following 5 steps which are illustrated below specifically as an example of the process for the synthesis of pyridoindole derivatives (IIIa).

Conventional Route:

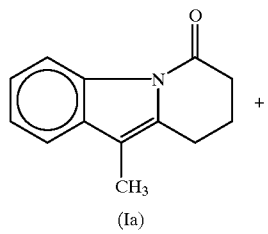

(Ia)

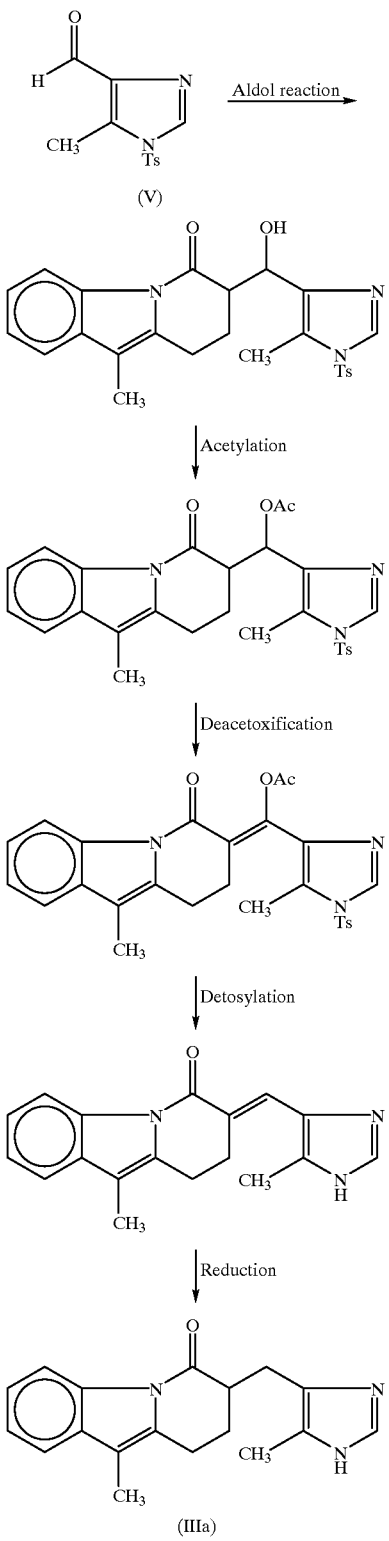

In the above described conventional processes, the object compound (IIIa) is obtained from the compound (Ia) by means of processes through five steps, which comprises an alkylation first being carried out through an aldol reaction with an aldehyde (V), followed by acetylation, deacetoxification, detosylation, and reduction to synthesize the compound (IIIa). Here, the yield from the compound (Ia)

to the object compound (IIIa) is 68%. The processes for producing the pyridoindole derivatives shown by the general formula (III) which are disclosed in the aforesaid Japanese Tokkyo Koho have drawbacks in the complicated processes due to the large number of steps, in the low yield, and in the higher cost, and so forth.

Furthermore, the aforesaid pyridoindole derivative is generally obtained as a racemic mixture. Moreover, the stereoisomers of said pyridoindole derivatives are generally obtained by the resolution process involving a reaction with an optically active reagent such as, for example, diparatoluoyltartaric acid or the like. However, the conventional optical resolution processes using diparatoluoyltartaric acid or the like have the drawback not only in the low yield but also in the use of a large amount of the solvent for the crystallization, and also are inavoidable to use chloroform which is in trouble for its safety.

DISCLOSURE OF INVENTION

The present invention provides a process for producing a pyridoindole derivative (III) or a salt thereof in one single step illustrated in the Process 1, shown below; which comprises a direct alkylation of a compound (I) or a salt thereof with an alkylating agent (II) or a salt thereof. This process is superior in it's simplicity and it's yield to the process disclosed in the aforesaid Japanese Kokai Tokkyo Koho.

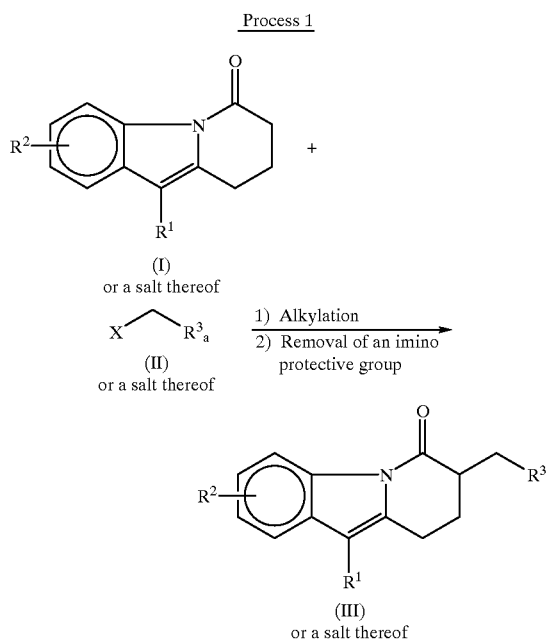

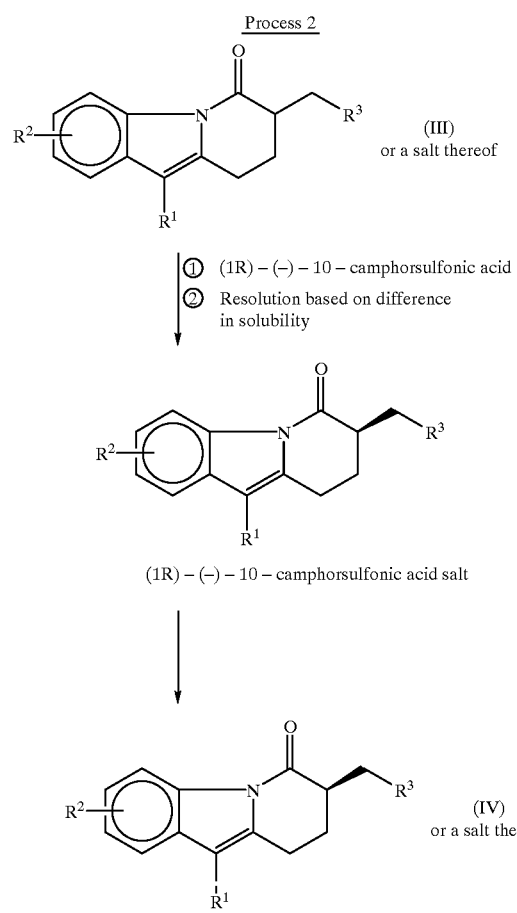

wherein $R^1$ is hydrogen, a lower alkyl group or a lower alkenyl group, $R^2$ is hydrogen, a lower alkyl group or a halogen, $R^3_a$ is an imidazolyl group substituted with an imino protective group, which may have a suitable substituent (s), $R^3$ is an imidazolyl group which may have a suitable substituent (s), and X is a halogen.

In addition, the present invention also provides a process for producing an optically active pyridoindole derivative (IV) or a salt thereof from a racemic mixture of the pyridoindole derivative (III) or a salt thereof by means of the following process, which is superior to the process in the aforesaid Japanese Kokai Tokkyo Koho at the point of it's yield and it's safety due to the unuse of harmful chloroform and so on.

In the above and subsequent descriptions of the present specification, suitable examples and illustrations of the various definitions which the present invention includes within the scope thereof are explained in detail as follows.

The term "lower" is intended to mean 1 to 6 carbon atoms, preferably 1 to 4 carbon atoms, unless otherwise indicated.

Suitable "lower alkyl" may include a straight or branched one having 1 to 6 carbon atom (s) such as methyl, ethyl, propyl, isopropyl, butyl, isobutyl, t-butyl, pentyl, benzyl, hexyl, preferably the one having 1 to 4 carbon atoms, and the like, in which the most preferred one is methyl, ethyl, or propyl.

Suitable "lower alkenyl" may include vinyl, 1-propenyl, allyl, 1-butenyl, 2-butenyl, 2-pentenyl, preferably the one having 2 to 4 carbon atoms, and the like, in which the most preferred one is allyl.

Suitable "halogen" may include fluorine, chlorine, bromine and iodine.

Suitable "imidazolyl" may include 1H-imidazol-1-yl, 1H-imidazol-2-yl, 1H-imidazol-4-yl and 1H-imidazol-5-yl.

Suitable "substituent (s)" in the term "imidazolyl which may have a suitable substituent (s)" and "imidazolyl substituted with an imino protective group, which may have a suitable substituent (s)" may include any group conventionally used in pharmacological fields such as the aforementioned lower alkyl or the like.

Suitable "imino protective group" may include a conventional one, in which the preferable example is acyl [e.g. N,N-di (lower) alkylsulfamoyl groups (e.g., N,N-dimethylsulfamoyl group, etc.), lower alkanesulfonyl groups (e.g., mesyl group, etc.), arenesulfonyl groups (e.g., tosyl group, etc.),etc], and the like wherein, a tosyl group (p-toluenesulfonyl group) is most preferable.

It is described below in detail that the process for producing pyridoindole derivative (III) or a salt thereof, and the process for the producing an optically active pyridoindole derivative (IV) or a salt thereof from a racemic mixture of a pyridoindole derivative (III) or a salt thereof, of the present invention.

Process 1

A compound (I) or a salt thereof is reacted with a base to form an enolate, the enolate is subjected to an alkylation reaction by using an alkylating agent (II) or a salt thereof, and thus obtained alkylated compound is subjected, without an isolation, to a removal reaction of the imino protective group, to obtain a pyridoindole derivative (III) or a salt thereof.

An appropriate base for use to form an enolate from the compound (I) or a salt thereof prior to the alkylation reaction, may include inorganic and organic bases such as, for example, alkali metals (e.g., lithium, sodium, potassium, etc.), alkaline earth metals (e.g., magnesium, calcium, etc.), alkali metal alkoxides (e.g., sodium methoxide, sodium ethoxide, potassium t-butoxide, etc.), alkali metal hexamethyldisilazit, and so forth.

In this alkylation reaction, the selection of the imino protective group and the halogen (X group) of the alkylating agent (II) or a salt thereof are important, since these influence the stability of the alkylating agent (II) or a salt thereof and the progress of the alkylation reaction.

From the perspective of stability of the alkylating agent (II) or salt thereof, the use of a tosyl group (p-toluenesulfonyl group) as the imino protective group and the use of chlorine as the halogen (X group) are most preferable.

When a tosyl group (p-toluenesulfonyl group) as the imino protective group and chlorine as the halogen (X group) in the alkylating agent (II) or a salt thereof are each used, the progress of the alkylation reaction is facilitated by the addition of sodium iodide to this alkylating agent in the presence of a suitable solvent while agitation at approximately 20° C., since the chlorate is converted into an iodate (halogen exchange).

The alkylation reaction is normally carried out in a conventional solvent, such as dioxane, tetrahydrofuran, diethyl ether, diisopropyl ether, chloroform, methylene chloride, ethylene chloride, N,N-dimethylformamide or any other desired organic solvent which does not exert an adverse effect on the reaction.

When the base used is in the form of a liquid, this may also serve as the solvent.

While there is no particular limitation with regard to reaction temperature, cooling is normally performed while the reaction is being carried out.

Following the alkylation reaction, by subjecting the alkylate obtained therefrom, without isolation to a removal reaction of an imino protective group to give a racemic mixture of pyridoindole derivative (III) or a salt thereof with the satisfactory yield.

As appropriate processes for removing the imino protective group, any conventional processes which are used for the removal of an imino protective group from an imidazolyl group, such as, hydrolysis, reduction, and so forth, may be exemplified.

With respect to a reduction, a chemical reduction by using an alkali metal borohydrides (e.g., sodium borohydride, etc.), a catalytic reduction by using a palladium catalysts (e.g., palladium—carbon, etc.), and the like may be exemplified With respect to a hydrolysis, this is preferably carried out in the presence of an acid or a base.

A suitable base may include, for example, inorganic bases such as alkali metal hydroxides (e.g., sodium hydroxide, potassium hydroxide, etc.), alkaline earth metal hydroxides (e.g., magnesium hydroxide, calcium hydroxide, etc.), alkali metal carbonates (e.g., sodium carbonate, potassium carbonate, etc.), alkaline earth metal carbonates (e.g., magnesium carbonate, calcium carbonate, etc.), alkali metal bicarbonates (e.g., sodium bicarbonate, potassium bicarbonate, etc.), alkali metal acetates (e.g., sodium acetate, potassium acetate, etc.), alkaline earth metal phosphates (e.g., magnesium phosphate, calcium phosphate, etc.), alkali metal hydrogenphosphates (e.g., disodium hydrogenphosphate, dipotassium hydrogenphosphate, etc.) and the like, and organic bases such as 1,5-diazabicyclo [4.3.0]nonan-5-one, 1,4-diazabicyclo[2.2.2]octane, 1,5-diazabicyclo[5.4.0]undecene-5 and the like. The hydrolysis using a base is preferably carried out in water, in a hydrophilic organic solvent, or in a mixture thereof.

A suitable acid may include organic acids (e.g., formic acid, acetic acid, propionic acid, etc.) and inorganic acids (e.g., hydrochloric acid, hydrobromic acid, sulfuric acid, etc.).

This hydrolysis is preferably carried out in an organic solvent, in water, or in the mixture solvent thereof.

The reaction temperature is not critical, the reaction can be normally carried out under cooling, at the room temperature, or under heating.

The reaction scheme of the process for producing (±)8, 9-dihydro-10-methyl-7-[(5-methyl-1H-imidazol-4-yl) methyl]pyrido[1,2-a]indol-6(7H)-one (IIa) is illustrated below.

Synthetic Route for Compound (IIIa) of the Present Invention:

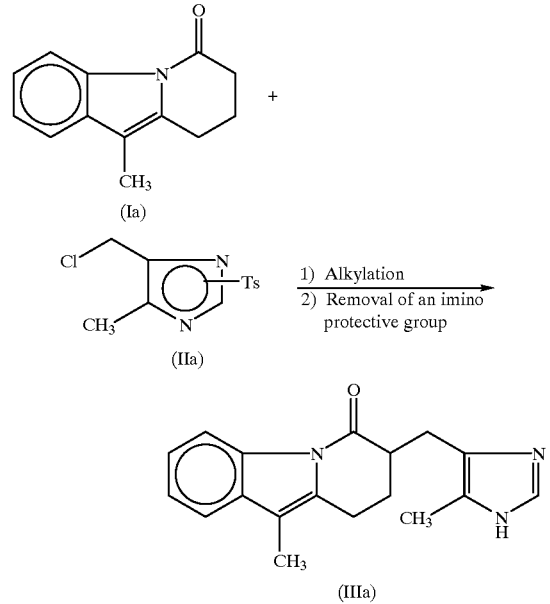

This invention provides a compound (IIIa) in high yield (88%) by using firstly a process for the synthesis of the alkylating agent (IIa), which had not been synthesized conventionally due to the problems with the stability, and secondly a direct alkylation of the compound (Ia). More specifically, this invention provides an improvement of reactivity of the compound (IIa) by using a halogen exchange reaction of the alkylating agent (IIa) with sodium iodide.

Process 2

A (±)isomer pyridoindole derivative (III) or a salt thereof is reacted with (1R)-(-)-10-camphorsulfonic acid (hereinafter referred to as (R)·CSA) to obtain a (+)isomer pyridoindole derivative·CSA salt and a (-)isomer pyridoindole derivative·CSA salt. The (+)isomer pyridoindole derivative·CSA salt and the (-)isomer pyridoindole derivative·CSA salt are resolved using their different solubilities in a solvent. As the solvent, one may use, for example, hydrous ethanol or the like. The optically active (+)isomer pyridoindole derivative (IV) can be obtained by desalting is the resolved (+)isomer pyridoindole derivative·CSA salt. Desalting is carried out in the presence of a base, e.g. sodium hydroxide. The resolved (+)isomer pyridoindole derivative·CSA salt is purified by recrystallization or the like prior to desalting. In addition, (+)isomer pyridoindole derivative yield is increased by racemizing the resolved (-)isomer pyridoindole derivative·CSA salt by means of a process in conventional use, e.g. a process indicated in the Examples described below, and again carrying out optical resolution.

The (+)isomer pyridoindole derivative (IV) may be converted to a suitable salt by means of a process in conventional way, e.g. a process indicated in the Examples described below. A suitable salt may include conventional nontoxic pharmaceutically acceptable salts; to wit a base or an acid addition salt. More specifically, they may include the salts of inorganic bases such as alkali metal salts (e.g., sodium salts, potassium salts, cesium salts, etc.), alkaline earth metal salts (e.g., calcium salts, magnesium salts, etc.), and ammonium salts; salts of organic bases such as organic amine salts (e.g., triethylamine salts, pyridine salts, picoline salts, ethanolamine salts, triethanolamine salts, dicyclohexylamine salts, N,N-dibenzylethylenediamine salts, etc.); salts of inorganic acids (e.g., hydrochloride, hydrobromide, sulfate, phosphate, etc.); organic carboxylate and organic sulfonates (e.g., formate, acetate, trifluoroacetate, maleate, tartrate, methanesulfonate, benzenesulfonate, p-toluenesulfonate, etc.); salts of basic amino acids and acidic amino acids (e.g., arginine, aspartic acid, glutamic acid, etc.); and so forth.

An appropriate salts of the object compound and the starting compound in Process 1 and Process 2 can be referred to the ones as mentioned above.

Below, we describe the present invention in further detail with reference to Preparations and Examples.

PREPARATION 1

4-chloromethyl-5-methyl-imidazole hydrochloride (100 g) was suspended in dimethylacetamide (400 ml), and p-toluenesulfonyl chloride (102.7 g) was added thereto while cooling over ice bath. N-methylmorpholine (151.4 g) was dropped therein under the interior temperature of 0–10° C. After completion of the adding, agitation at the same temperature for an additional 30 minutes was continued. After the reaction is completed, ethyl acetate (1,000 ml) and water (500 ml) were added to the reaction solution and the crystals were thoroughly dissolved, and thereafter liquid fractions were separated. The water layer was extracted with ethyl acetate (300 ml). Ethyl acetate fractions were combined, and were washed twice, with 10% aqueous citric acid (300 ml) and 20% brine (1,000 ml). The solution was dried with anhydrous magnesium sulfate, and then the solvent was removed under vacuum. To the residue, n-heptane (500 ml) was added, cooled over ice bath, and then precipitated crystals were collected by filtration. They were dried overnight under vacuum to obtain the mixture of 1-tosyl-4-chloromethyl-5-methyl-imidazole and 3-tosyl-4-chloromethyl-5-methyl-imidazole as white crystals (134.7 g).

1-Tosyl-4-chloromethyl-5-methyl-imidazole NMR (CDCl$_3$, δ): 2.28 (3H, s), 2.46 (3H, s), 4.46 (2H, s), 7.38 (2H, d), 7.78 (2H, d), 8.09 (1H, s)

3-Tosyl-4-chloromethyl-5-methyl-imidazole NMR (CDCl$_3$, δ): 2.21 (3H, s), 2.44 (3H, s), 4.80 (2H, s), 7.36 (2H, d), 7.85 (2H, d), 8.07 (1H, s)

EXAMPLE 1

Under nitrogen stream, sodium iodide (97.8 g) and a mixture of 1-tosyl-4-chloromethyl-5-methyl-imidazole and 3-tosyl-4-chloromethyl-5-methyl-imidazole (186 g) in tetrahydrofuran (1,000 ml) were agitated vigorously at an interior temperature of 18~23° C. for 2 hours, and after carrying out halogen exchange, the reaction solution was cooled to an interior temperature of −40~−50° C. In a separate reaction vessel, under nitrogen stream, 8,9-dihydro-10-methyl-pyrido[1,2-a]indol-6(7H)-on (100 g) was dissolved in tetrahydrofuran (900 ml), cooled to −40~−50° C. and a 1.35 N solution of lithium hexamethyldisilazit/tetrahydrofuran-n-hexane (409 ml) were dripped therein while maintaining at same temperature. After dripping was completed, the reaction was carried out under the agitate at same temperature for an additional 30 minutes and thereafter the solution was dripped into the halogen exchange reaction solution prepared above while maintaining a temperature of −40~−50° C. The reaction was carried out at the same temperature for 15 minutes, and acetic acid (12.1 g) was added thereto. An interior temperature was raised to 5~10° C., then 5% aqueous sodium thiosulfate (1,000 ml) was added thereto, and the upper layer was collected. It was concentrated under vacuum until the volume is approximately 800 ml. After the concentrating is completed, the mixture of methanol (400 ml), water (200 ml), and concentrated hydrochloric acid (100 ml) was added thereto, and were agitated for 3 hours after the interior temperature was raised to 48~53° C. After the reaction is completed, the solution was adjusted to pH 7.8–8.2 with 12% aqueous sodium hydroxide solution, and was concentrated under vacuum until volume is approximately 800 ml. Ethyl acetate (300 ml) was added thereto, adjusted to pH 10.5±0.2 with 12% aqueous sodium hydroxide, thereafter was cooled to a temperature of not higher than 10° C., and the precipitated crystals were collected by filtration. They were washed with ethyl acetate (300 ml) and water (500 ml), and then dried overnight under vacuum to obtain (±)8,9-dihydro-10-methyl-7-[(5-methyl-1H-imidazol-4-yl)methyl]pyrido[1,2-a]indol-6(7H)-one as yellowish-brown crystals (129.0 g).

NMR (CDCl$_3$, δ): 1.83–1.97 (1H, m), 2.15 (3H, 1H, d+m), 2.22 (3H, d), 2.79–3.14 (5H, m), 7.3 (2H, m), 7.3–7.4 (2H, m+s), 8.45 (1H, m)

EXAMPLE 2

(1) The mixture of (±)8,9-dihydro-10-methyl-7-[(5-methyl-1H-imidazol-4-yl)methyl]pyrido[1,2-a]indol-6(7H)-one (50 g) and (1R)-(-)-10-camphorsulfonic acid (CSA) (42.7 g) were dissolved 5% hydrous ethanol (250 ml) under reflux. After cooling, at the interior temperature of 33° C. the seed crystals (0.1 g) were added thereto, and the agitate at 20~30° C. for 20 hr caused to thoroughly precipitate (+)8,9-dihydro-10-methyl-7-[(5-methyl-1H-imidazol-4-yl)methyl]pyrido[1,2-a]indol-6(7H)-one·CSA salt and (−)8,9-dihydro-10-methyl-7-[(5-methyl-1H-imidazol-4-yl)methyl]pyrido[1,2-a]indol-6(7H)-one·CSA salt. 5% hydrous ethanol (100 ml) was added thereto and the mixture was agitated at the same temperature for 1 hr, 5% hydrous ethanol (50 ml) was added thereto and the mixture was agitated for 1 hr, 5% hydrous ethanol (100 ml) was added thereto and the mixture was agitated for 1 hr, and 5% hydrous ethanol (50 ml) was added thereto and the mixture was agitated for 1 hr, and (−)8,9-dihydro-10-methyl-7-[(5-methyl-1H-imidazol-4-yl) methyl]pyrido[1,2-a]indol-6(7H)-one·CSA salt were redissolved. The solution was allowed to stand overnight, thereafter the crystals were collected by filtration, washed with 50 ml of ethanol, and thereafter dried overnight under vacuum to obtain (+)8,9-dihydro-10-methyl-7-[(5-methyl-1H-imidazol-4-yl)methyl]pyrido[1,2-a]indol-6(7H)-one·CSA salt as white coarse crystals.

Yield=22.7 g. Percent yield 25.3%.

(+)isomer CSA salt: (−)isomer CSA salt=96.0:4.0 (here and below, LC measurement values as determined by the liquid chromatographic process described below).

(2) Purification (+)8,9-dihydro-10-methyl-7-[(5-methyl-1H -imidazol-4-yl)methyl]pyrido[1,2-a]indol-6 (7H)-one·CSA salt (22.0 g) obtained above was dissolved in ethanol (110 ml) under reflux. After cooling, it was agitated for 3 hr at an interior temperature of 20~30° C., thereafter the precipitated crystals were collected by filtration and washed with ethanol (22 ml). They were dried overnight under vacuum to obtain (+)8,9-dihydro-10-methyl-7-[(5-methyl-1H-imidazol-4-yl)methyl] pyrido[1,2-a]indol-6(7H)-one·CSA salt as white crystals.

Yield=19.9 g. Percent yield=90.5%.

Isomer ratio: (+)isomer CSA salt: (−)isomer CSA salt= 99.7:0.3 (LC measurement values).

(3) The mother liquor and the washings were combined, water (500 ml) was added thereto, and were adjusted to pH8.9 with 8% aqueous sodium hydroxide (approx. 50 ml) at an interior temperature of 20~30° C. After agitating for 1 hr, the precipitated crystals were collected by filtration, washed with water (150 ml), and thereafter were dried overnight under vacuum to recover (±)8,9-dihydro-10-methyl-7-[(5-methyl-1H-imidazol-4-yl)methyl]pyrido[1,2-a]indol-6(7H)-one as light yellow crystals.

Yield=34.8 g. Percent yield=69.5%.

Isomer ratio: (+)isomer: (−)isomer=34.3:65.7 (LC measurement values).

(4) Re-racemization (±)8,9-dihydro-10-methyl-7-[(5-methyl-1H-imidazol-4-yl)methyl]pyrido[1,2-a]indol-6(7H)-one (30.0 g) [isomer ratio: (+):(−)=34.3:65.7] obtained above was suspended in toluene (300 ml), and 1,8-diazabicycloundecene (DBU) (15.7 g) was added thereto, and was refluxed for 10 hr. It was cooled to an interior temperature of 20~30° C., and the crystals were collected by filtration, washed with toluene (30 ml), and thereafter were dried overnight under vacuum and re-racemized to obtain (±)8,9-dihydro-10-methyl-7-[(5-methyl-1H-imidazol-4-yl)methyl]pyrido[1,2-a]indol-6(7H)-one.

Yield=27.4 g. Percent yield=91.2%. Isomer ratio: (+)isomer: (−)isomer 48.1:51.9 (LC measurement values).

(5) According to a similar manner to that of Example 2-(1), (±)8,9-dihydro-10-methyl-7-[(5-methyl-1H-imidazol-4-yl) methyl]pyrido[1,2-a]indol-6(7H)-one·CSA salt was obtained by using (±)8,9-dihydro-10-methyl-7-[(5-methyl-1H-imidazol-4-yl)methyl]pyrido[1,2-a]indol-6(7H)-one (20.0 g).

Yield=8.00 g. Percent yield=22.5%.

Isomer ratio: (+)isomer CSA salt: (−)isomer CSA salt= 95.6:4.4 (LC measurement values).

(6) Purification

According to a similar manner to that of Example 2-(2), (+)8,9-dihydro-10-methyl-7-[(5-methyl-1H-imidazol-4-yl) methyl]pyrido[1,2-a]indol-6(7H)-one·CSA salt (7.00 g) obtained according to the manner of Example 2-(5), was recrystallized with ethanol and purified to obtain (+)8,9-dihydro-10-methyl-7-[(5-methyl-1H-imidazol-4-yl)methyl] pyrido[1,2-a]indol-6(7H)-one·CSA salt.

Yield=6.33 g. Percent yield=90.4%.

Isomer ratio: (+)isomer CSA salt: (−)isomer CSA salt= 99.7:0.3 (LC measurement values).

(7) (+)8,9-dihydro-10-methyl-7-[(5-methyl-1H-imidazol-4-yl)methyl]pyrido[1,2-a]indol-6(7H)-one·CSA salt (15.0 g) was suspended in methanol (45 ml) and water (105 ml), and adjusted to pH10.6 with 8% aqueous sodium hydroxide (10 ml) at an interior temperature of 20~30° C. It was agitated for 1 hr at the same temperature, thereafter the crystals were collected by filtration, washed with water (45 ml), and thereafter dried overnight under vacuum to obtain (+)8,9-dihydro-10-methyl-7-[(5-methyl-1H-imidazol-4-yl)methyl] pyrido[1,2-a]indol-6(7H)-one.

Yield=8.59 g. Percent yeild=102.6%.

(8) (+)8,9-dihydro-10-methyl-7-[(5-methyl-1H-imidazol-4-yl)methyl]pyrido[1,2-a]indol-6(7H)-one (8.0 g) was dissolved in ethanol (80 ml) and water (72 ml), and 6 N hydrochloric acid (8 ml) was added thereto at an interior temperature of 20~30° C., and it was agitated at the same temperature for 1 hr. It was clarified by filtration, and the container and so forth was washed with ethanol (8 ml). Water (272 ml) was dripped therein at a temperature of 20~30° C. over the course of 20 min, and the seed crystals (0.016 g) were added thereto, and it was agitated at the same temperature for 3 hr, cooled to 0~5° C., and agitated for 3 hr. The precipitated crystals were collected by filtration, washed with water (32 ml), and thereafter dried overnight under vacuum to obtain (+)8,9-dihydro-10-methyl-7-[(5-methyl-1H-imidazol-4-yl)methyl]pyrido[1,2-a]indol-6(7H)-one·hydrochloride.

Yield=7.38 g. Percent yield=82.0%.

Optical Resolution Liquid Chromatographic LC Conditions

Column: CHIRAL-AGP (mfd. by Chromtech, Sweden)

Internal diameter 4 mm, length 100 mm, bead diameter 5 micron

Column temperature: 35° C.

Mobile phase: 30% hydrous acetonitrile, pH 7

$Na_2HPO_4 \cdot 12H_2O$: 2 g

KH2PO4: 0.5 g

Distilled water: 700 ml

Acetonitrile: 300 ml

Flow rate: 0.8 ml/mm; Detection wavelength: 254 nm (+)isomer: Approx. 2.5 min; (−)isomer: Approx. 4 min

EXAMPLE 3

(1) (±)8,9-dihydro-10-methyl-7-[(5-methyl-1H-imidazol-4-yl)methyl]pyrido[1,2-a]indol-6(7H)-one (100 g), (1R)-(−)-10-camphorsulfonic acid monohydrate (85.3 g), and radiolite (1 g) in ethanol (1,000 ml) were heated under reflux. It was cooled to 35° C., and 0.2 g of seed crystals were added thereto, thereafter it was agitated at an interior temperature of 20~30° C. for 3 hr, and after ethanol (1,000 ml) was added therto, it was agitated overnight at 20~30° C. The following day, water (25 ml) was added thereto and it was agitated for 1 hr at 20~30° C., and after the temperature was raised to 33~37° C., it was agitated for 30 min. It was cooled to 20~30° C., thereafter the precipitated crystals were collected by filtration, washed with ethanol (100 ml), and dried overnight under vacuum to obtain (+)8,9-dihydro-10-methyl-7-[(5-methyl-1H-imidazol-4-yl)methyl]pyrido[1,2-a]indol-6(7H)-one·CSA salt as colorless coarse crystals.

Yield=53.9 g (including seed crystals+radiolite). Percent yield=28%.

(+)isomer CSA salt: (−)isomer CSA salt=96.0:4.0 (LC measurement values).

NMR (CDCl$_3$, δ): 0.80 (3H, s), 1.03 (3H, s), 1.8 (lH, m), 1.9–2.2 (2H+2H+2H+1H, m), 2.10 (3H, s), 2.32 (3H, s), 2.5–3.1 (2H+2H+1H+1H, m), 3.3–3.5 (2H, m), 7.2 (2H, m), 7.4 (1H, m), 8.3 (1H, m), 8.49 (1H, s), 13.8 (1H, broad).

(2) Under vacuum, the above mother liquor was concentrated to approximately 1,000 ml, and 1,000 ml of water was added thereto, thereafter it was adjusted to pH13, and the precipitated crystals were collected by filtration, and were dried under vacuum to recover (±)8,9-dihydro-10-methyl-7-[(5-methyl-1H-imidazol-4-yl)methyl]pyrido[1,2-a]indol-6(7H)-one.

Yield=73.8 g.

(3) Re-racemization 38.3 g of DBU and 73.8 g of the recovered crystals (73.8 g) obtained according to a manner of Example 3-(2) in toluene (738 ml) were heated under reflux for 3 hr. After cooling, the crystals were collected by filtration at an interior temperature of 20~30° C., washed with toluene (150 ml) and water (150 ml), and thereafter dried overnight under vacuum to obtain (±)8,9-dihydro-10-methyl-7-[(5-methyl-1H-imidazol-4-yl)methyl]pyrido[1,2-a]indol-6(7H)-one as crystals.

Yield=65.3 g.

(+)Isomer CSA salt: (−)isomer CSA salt=49.0:51.0 (LC measurement values).

(4) By using (±)8,9-dihydro-10-methyl-7-[(5-methyl-1H-imidazol-4-yl)methyl]pyrido[1,2-a]indol-6(7H)-one (65.3 g) obtained according to a manner of Example 3-(2), according to a similar manner to that of Example 3-(1), (+)8,9-dihydro-10-methyl-7-[(5-methyl-1H-imidazol-4-yl)methyl] pyrido[1,2-a]indol-6(7H)-one·CSA salt as coarse crystals was obtained.

Yield=35.2 g. Percent yield=18.3% (overall yield from (±)8,9-dihydro-10-methyl-7-[(5-methyl-1H-imidazol-4-yl) methyl]pyrido[1,2-a]indol-6(7H)-one=46.3%).

(+)Isomer CSA salt: (−)isomer CSA salt=96.0:4.0 (LC measurement values).

(5) Purification

The mixture of (+)8,9-dihydro-10-methyl-7-[(5-methyl-1H-imidazol-4-yl)methyl]pyrido[1,2-a]indol-6(7H)-one·CSA salt (53.9 g) obtained according to a manner of Example 3-(1) and (±)8,9-dihydro-10-methyl-7-[(5-methyl-1H-imidazol-4-yl)methyl]pyrido[1,2-a]indol-6(7H)-one·CSA salt (35.2 g) obtained according to a manner of Example 3-(4) was dissolved in ethanol (446 ml) by heating under reflux. The powdered carbon (1.8 g) was added thereto and refluxed again, thereafter the radiolite and the powdered carbon was collected by filtration while hot. The filtrate was cooled to room temperature, thereafter the precipitated crystals were collected by filtration to obtain (+)8,9-dihydro-10-methyl-7-[(5-methyl-1H-imidazol-4-yl)methyl]pyrido[1,2-a]indol-6(7H)-one·CSA salt as colorless crystals.

Yield=75.2 g. Percent yield=86%.

(+)Isomer CSA salt: (−)isomer CSA salt=99.6:0.4 (LC measurement values).

(6) (+)8,9-dihydro-10-methyl-7-[(5-methyl-1H-imidazol-4-yl)methyl]pyrido[1,2-a]indol-6(7H)-one·CSA salt (100 g) was suspended in the mixture of methanol (300 ml) and deionized water (700 ml), and adjusted to pH11.5–12.5 with 24% aqueous sodium hydroxide, the crystals were collected by filtration, washed with water, and dried to obtain (+)8,9-dihydro-10-methyl-7-[(5-methyl-1H-imidazol-4-yl) methyl]pyrido[1,2-a]indol-6(7H)-one as white crystals.

Yield=53.6 g. Percent yield=96%.

(7) (+)8,9-dihydro-10-methyl-7-[(5-methyl-1H-imidazol-4-yl)methyl]pyrido[1,2-a]indol-6(7H)-on (100 g) was suspended in the mixture of ethanol (300 ml) and deionized water (300 ml), and 6 N hydrochloric acid (100 ml) was added thereto at an interior temperature of not less than 30° C. After the addition thereof, it was heated to an interior temperature of 65~75° C. and the precipitated crystals were dissolved. After the dissolution, it was clarified by filtration, and the filtration vessel and so forth were washed with 200 ml of deionized water. The filtrate and the washings was combined, cooled to a temperature of not higher than 10° C., and the precipitated crystals were collected by filtration, washed with water, and dried to obtain (+)8,9-dihydro-10-methyl-7-[(5-methyl-1H-imidazol-4-yl)methyl]pyrido[1,2-a]indol-6(7H)-one·hydrochloride as white crystals.

Yield=104.6 g. Percent yield=93%.

We claim:

1. A process for producing a pyridoindole compound of the formula:

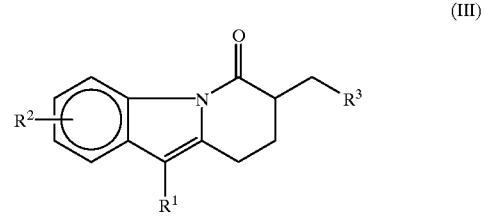

(III)

where $R^1$ is hydrogen, a lower alkyl group or a lower alkenyl group, $R^2$ is hydrogen, a lower alkyl group or halogen, and $R^3$ is an imidazolyl group optionally substituted by a lower alkyl moiety, or a salt thereof, by reacting a compound of the formula:

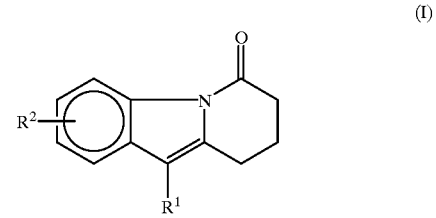

(I)

where $R^1$ and $R^2$ are respectively as indicated above, or a salt thereof with a compound of the formula:

(II)

where $R_a^3$ is an imidazolyl group substituted with an imino protective group, optionally substituted by a lower alkyl moiety, and X is halogen, or a salt thereof and then subjecting to a removal reaction of an imino protective group.

2. A process for producing a pyridoindole compound or a salt thereof of claim 1, wherein $R^1$ is a lower alkyl group, $R^2$ is hydrogen, $R^3$ is an imidazolyl group substituted with a lower alkyl group, and $R_a{}^3$ is an imidazolyl group substituted with an imino protective group, optionally substituted by a lower alkyl group.

3. A process for producing an optically active pyridoindole derivative of the formula:

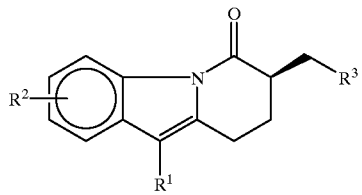

(IV)

where $R^1$ is hydrogen, a lower alkyl group or a lower alkenyl group, $R^2$ is hydrogen, a lower alkyl group or halogen, and $R^3$ is an imidazolyl group optionally substituted by a lower alkyl moiety, or a salt thereof, by reacting a racemic mixture of a pyridoindole derivative of the formula:

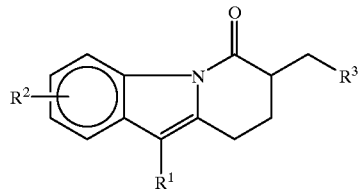

(III)

where $R^1$, $R^2$, and $R^3$ are respectively as indicated above, or a salt thereof with (1R)-(−)-10-camphorsulfonic acid.

4. A process for producing an optically active pyridoindole derivative or salt thereof of claim 3, wherein $R^1$ is a lower alkyl group, $R^2$ is hydrogen, and $R^3$ is an imidazolyl group optionally substituted by a lower alkyl.

* * * * *